US012064457B2

(12) United States Patent
Motte et al.

(10) Patent No.: US 12,064,457 B2
(45) Date of Patent: Aug. 20, 2024

(54) THERAPEUTIC USES OF AN INSECT POWDER

(71) Applicant: YNSECT, Evry-Courcouronnes (FR)

(72) Inventors: Constant Motte, Hem (FR); Benjamin Armenjon, Paris (FR); Antoine Hubert, Alfortville (FR); Nathalie Berezina, Paris (FR)

(73) Assignee: YNSECT, Evry-Courcouronnes (FR)

( * ) Notice: Subject to any disclaimer, the term of this patent is extended or adjusted under 35 U.S.C. 154(b) by 0 days.

(21) Appl. No.: 17/376,573

(22) Filed: Jul. 15, 2021

(65) Prior Publication Data

US 2021/0338743 A1 Nov. 4, 2021

Related U.S. Application Data

(62) Division of application No. 16/478,240, filed as application No. PCT/FR2018/050119 on Jan. 17, 2018.

(30) Foreign Application Priority Data

Jan. 18, 2017 (FR) ...................................... 1750390
Jun. 30, 2017 (FR) ...................................... 1756099

(51) Int. Cl.
| | | |
|---|---|---|
| A61K 35/64 | (2015.01) | |
| A23K 10/20 | (2016.01) | |
| A23K 20/147 | (2016.01) | |
| A23K 20/163 | (2016.01) | |
| A23K 40/10 | (2016.01) | |
| A23K 50/80 | (2016.01) | |

(52) U.S. Cl.
CPC .............. *A61K 35/64* (2013.01); *A23K 10/20* (2016.05); *A23K 20/147* (2016.05); *A23K 20/163* (2016.05); *A23K 40/10* (2016.05); *A23K 50/80* (2016.05)

(58) Field of Classification Search
CPC ...................................................... A61K 35/64
See application file for complete search history.

(56) References Cited

U.S. PATENT DOCUMENTS

2017/0354178 A1  12/2017  Armenjon et al.
2018/0000121 A1   1/2018  Armenjon et al.

FOREIGN PATENT DOCUMENTS

| CN | 103815167 | 5/2014 |
| CN | 103815168 A | 5/2014 |
| CN | 105106753 | 12/2015 |
| CN | 105475679 | 4/2016 |
| CN | 106071368 | 11/2016 |
| CN | 106071395 | 11/2016 |
| WO | WO 2016108036 | 7/2016 |
| WO | WO 2016108037 | 7/2016 |

OTHER PUBLICATIONS

English machine translation of Gao, CN106071368 A, 2016.*

(Continued)

*Primary Examiner* — Rosanne Kosson
(74) *Attorney, Agent, or Firm* — Panitch Schwarze Belisario & Nadel LLP; Erin M. Dunston (57) ABSTRACT

The invention relates to a Coleoptera powder for using in the treatment of vibriosis, which particularly affects the white shrimp.

8 Claims, 2 Drawing Sheets

(56) References Cited

OTHER PUBLICATIONS

Bryning et al., Identification of Sex Pheromone from Male Yellow Mealworm Beetles, 31(11) Journal of Chemical Ecology 2721-2730 (Nov. 2005).
Gasco et al., Tenebrio molitor meal in diets for European sea bass (*Dicentrarchus labrax* L.) juveniles: Growth performance, whole body composition and in vivo apparent digestibility, 220 Animal Feed Science and Technology 34-45 (2016).
Yang et al., Nutritional Composition and Protein Quality of the Edible Beetle Holotrichia parallela, 14(139) J. Insect Sci. 1-4 (2014).
International Search Report (with English translation) and Written Opinion issued in corresponding International Patent Application No. PCT/FR2018/050119, 13 pages (Apr. 17, 2018).
Bovera et al., *Yellow mealworm larvae (Tenebrio molitor, L.) as a possible alternative to soybean meal in broiler diets*, 56(5) British Poultry Science 569-575 (2015).
Cheng Donghai et al., *Effects of Dietary Protein Level and Animal Protein Sources on the Survival and Growth of Procambarus clarkii*, 40(22) Journal of Anhui Agri. 11311-11313 (2012) (English abstract).
Shujiang et al., *Studies on the Induction of Tenebrio molitor Antibacterial Peptides and Their Inhibitory Effects on Important Aquatic Bacteria*, 1 Chinese Master's Theses Full-Text Databases-Agricultural Science and Technology D052-50 (Jan. 2013).
Wang et al., *The protective effect of chitn and chitosan against Vibrio alginolyticus in white shrimp Litopenaeus Vannamei*, 19(3) FISH & Shellfish Immunology 191-204 (Sep. 2005).
Wright et al., *Optimization of Depuration-based Strategies using Chitosan Microparticules to Reduce Vibrio parahaemolyticus in the Eastern Oyster (Crassostrea virginica)*, Shellfish Processing 1-23 (Aug. 31, 2014).
Zhen-Jie et al., *The Effect of Tenebrio molitor Powder and Shell on Penaeus vannamei Boone's Major Non-specific Immunity Indexes*, 29(2) Chinese Journal of Fisheries 1-4 (Apr. 2016) (English abstract).
TKDL:AM05/2494A, Title of Traditional Knowledge Resource: Kaluthai Vandukku Murivu, Kowledge Known Since 1000 Years (1879).
TKDL:JA6/488E, Title of Traditional Knowledge Resource: Nuskha-e- Naqoo, Knowledge Known Since 100 Years (1926).
TKDL: AA4/227A, Title of Traditional Knowledge Resource: Dawa-e Doodi, Knowledge Known Since 1000 Years (1978).
TKDL: GP01/271, Title of Traditional Knowledge Resource: Aya Kalangu, Knowledge Known Since 500 Years (1979).

\* cited by examiner

THERAPEUTIC USES OF AN INSECT POWDER

CROSS-REFERENCE TO RELATED APPLICATIONS

This application is a Divisional Application of U.S. patent application Ser. No. 16/478,240, filed on Jul. 16, 2019, which is a U.S. National Stage Application pursuant to 35 U.S.C. § 371 of International Patent Application PCT/FR2018/050119, filed on Jan. 17, 2018, and published as WO 2018/134524 on Jul. 26, 2018, which claims priority to French Patent Application No. 1756099, filed on Jun. 30, 2017, and French Patent Application No. 1750390, filed on Jan. 18, 2017, all of which are incorporated herein by reference in their entireties for all purposes.

The present invention relates to an insect powder and to the use thereof, in particular in aquaculture.

Aquaculture is today one of the most dynamic sectors in the food industry. Aquaculture relates in particular to the production of fish (pisciculture), shellfish (shellfish farming) or also crustaceans (crayfish culture and shrimp farming).

The high demand for fish has resulted in a significant increase in the price of feed intended for rearing fish, shellfish and crustaceans.

One of the products most used in aquaculture is fishmeal. It is an easily-digestible meal which is very rich in animal proteins (rich in lysine- and methionine-type amino acids). A growing demand accompanied by a limited supply has resulted in a significant increase in its price, creating a risk to the sustainable growth of aquaculture. Thus, there is a high demand for alternative sources of high-quality, and, so far as possible renewable, proteins for aquaculture feeds.

Insect powders or insect meal offer natural replacement protein sources, as well as the possibility of mass production with a minimal ecological footprint. In particular, certain beetles such as *Tenebrio molitor* have the benefit of being suitable for intensive mass production.

Furthermore, farmed fish, shellfish or crustaceans, due to grouping together a large number of individuals in the rearing basins, are very often subject to epidemics of bacterial origin such as for example *Vibrio parahaemolyticus* which decimated over 70% of the population of farmed shrimps in certain regions.

*Vibrio parahaemolyticus* is a bacterium that mainly infects shellfish (in particular oysters and mussels), crustaceans (in particular shrimps) and fish. This bacterium can be transmitted to humans, in particular when infected shellfish, crustaceans or fish are eaten, and causes enteritis and gastroenteritis.

There is therefore a need for an effective means to prevent the risk of infections and/or to effectively combat bacterial epidemics.

To this end, the inventors have demonstrated that administration of insect powder makes it possible to prevent and cure bacterial infections.

Thus, the present invention also relates to an insect powder for use as a medicament.

By "insect powder", is meant a composition, in the form of particles, prepared solely from insects and optionally water.

The residual moisture level in the insect powder is comprised between 2 and 15%, preferably between 5 and 10%, more preferentially between 4 and 8%. This moisture level can for example be determined according to the method originating from EC Regulation 152/2009 of 27 Jan. 2009 (103° C./4 h).

It will be noted that, in the context of the present application, and unless otherwise stipulated, the ranges of values indicated are to be understood as including boundaries.

Throughout the entire application, when no date is specified for a regulation, a standard or a directive, it is the regulation, standard or directive in force on the date of filing.

When the insect powder is ground to a particle size acceptable for human or animal nutrition, the latter can be referred to as "insect meal". By "particle size acceptable for human or animal nutrition", is meant a particle size comprised between 100 µm and 1.5 mm, preferentially comprised between 300 µm and 1 mm, more preferentially between 500 and 800 µm.

By "insects" is meant in particular Coleoptera, Diptera, Lepidoptera, Orthoptera, Hymenoptera, Dictyoptera, grouping together in particular the Blattoptera, including Isoptera, and the Mantoptera, Phasmoptera, Hemiptera, Heteroptera, Ephemeroptera and Mecoptera, preferably, Coleoptera, or mixtures thereof.

Preferentially, the beetles preferred according to the invention belong to the families of the Tenebrionidae, Melolonthidae, Dermestidae, Coccinellidae, Cerambycidae, Carabidae, Buprestidae, Cetoniidae, Dryophthoridae, or mixtures thereof.

More preferentially, they are the following beetles: *Tenebrio molitor, Alphitobius diaperinus, Zophobas morio, Tenebrio obscurus, Tribolium castaneum* and *Rhynchophorus ferrugineus*, or mixtures thereof.

Advantageously, the insect powder is obtained from the larval stage of the insect species mentioned above.

The insect powder according to the invention can be administered to humans or animals with a view to a preventive or curative treatment.

This insect powder makes it possible in particular to combat effectively the bacterial infections caused by bacteria of the *Vibrio* species genus, in particular bacterial infections caused by *Vibrio parahaemolyticus*.

In fact, when white shrimps infected with *Vibrio parahaemolyticus* are fed with insect powder rather than fishmeal, the mortality rate of the white shrimps is thereby limited. This probably results from strengthening of the immune defences of the white shrimps, due to stimulation of their immune system and/or to better development of the hepatocyte cells thereof (see Example 4 hereinafter).

More particularly, the invention relates to an insect powder for use in the treatment of vibriosis.

By "vibriosis" is meant all bacterial infections caused by bacteria of the *Vibrio* spp genus, belonging to the family Vibrionaceae, bacteria living in water. As indicated above, these bacteria are pathogenic to humans (being capable of causing serious infections) and/or to animals, in particular aquatic animals, thus being able to infect humans through their nutrition.

Preferably, these bacteria are *Vibrio aestuarianus*, responsible for oyster disease, *Vibrio parahaemolyticus*, responsible for enteritis and gastroenteritis, or *Vibrio splendidus* responsible for infectious disease in the cupped oyster. Preferably, the insect powder is intended for use in the treatment of vibriosis caused by *Vibrio parahaemolyticus*.

More particularly, the insect powder can be used in the treatment of vibriosis in molluscs and crustaceans.

By "molluscs" is meant an invertebrate animal with a soft body, consisting of a head, a foot and a visceral mass. Among the seven classes of molluscs, there may be mentioned three main branches: the gastropods, the bivalves and the cephalopods.

The gastropods group together in particular snails, slugs or also limpets. The bivalves group together in particular mussels, oysters or also clams. The cephalopods group together in particular octopuses, squids or also cuttlefish.

The molluscs to which the invention relates can be land animals or aquatic animals, preferably aquatic. By "aquatic" is meant freshwater animals or marine animals, preferably marine.

Preferably, the molluscs to which the invention relates belong to the groups of the bivalves comprising in particular the Pafaeotaxodonta, Cryptodonta, Pteriomorphia, Palaeoheterodonta, Heterodonta and Anomalodesmata.

Preferentially, the molluscs are selected from the Mytilida (mussels) and the Ostreida (oysters). The Ostreida group together in particular the *Ostrea*, the *Crassostrea* (cupped oysters), the *Ostreola* (flat oysters) or also the Saccostrea.

In particular, the mollusc species concerned are: *Mytilus edulis, Mytilus galloprovincialis, Tapes rhomboides* (banded carpet shell), *Venerupis decussata* (cross-cut carpet shell), *Venerupis philippinarum* (Japanese carpet shell), *Venerupis aurea* (golden carpet shell), *Corbicula fluminea* (Asiatic clam), *Ostrea edulis* (European flat oyster), *Crassostrea angulata* (Portuguese oyster), *Crassostrea gigas* (Japanese oyster), *Ostreola conchaphila* (Olympia oyster), *Crassostrea virginica* (American oyster or Virginia oyster).

By "crustaceans" is meant animals the body of which is covered by an exoskeleton of chitin and protein called exocuticle, which is often impregnated with calcium carbonate. This group comprises animals of variable sizes belonging to the lower classes such as the Branchiopoda, Cephalocarida, Malacostraca, Maxillopoda, Ostracoda, Remipedia.

Even more preferentially, the species of crustaceans to which the invention relates belong to the order of the Decapoda.

By "Decapoda" is meant crustaceans having 5 pairs of legs. The species of Decapoda are grouped together in two sub-classes: the *Dendrobranchiata* and the Pleocyemata.

Among the *Dendrobranchiata*, there may be mentioned, by their common name, the prawns belonging to the Penaeoidea Rafinesque superfamily.

Among the Pleocyemata, there may be mentioned, by their common name, the squat lobsters belonging to the infraorder of the Anomura, the crabs belonging to the subsection of the Heterotremata, or the infraorders of the Brachyura or the Paguroidea, the shrimps belonging to the infraorder Caridea, the crayfishes and the lobsters belonging to the infraorder of the Astacidea or also spiny lobsters belonging to the infraorder of the Chelata.

Preferably, the crustaceans to which the invention relates are shrimps. The shrimps may be marine or freshwater species. Advantageously, they are species of shrimps suitable for shrimp farming or freshwater farming.

Advantageously, the species of shrimps to which the invention relates belong to the family Penaeidae and in particular to the genus *Penaeus*.

Preferentially, the species of shrimps to which the invention relates are the following: the Pacific white shrimp (*Litopenaeus vannamei*), the Asian tiger shrimp (*Penaeus monodon*), the blue shrimp (*Penaeus stylirostris*), the fleshy prawn (*Penaeus chinensis*), the imperial prawn or kuruma prawn (*Penaeus japonicus*), the Indian prawn (*Penaeus indicus*), the banana prawn (*Penaeus merguiensis*), the akiami paste shrimp (*Metapenaeus* spp) and the giant river prawn (*Macrobrachium rosenbergii*), also preferably *Litopenaeus vannamei*.

Shrimps have several stages of development: three larval stages, namely the Nauplius, Zoea, Mysis stages, then they metamorphose into post-larvae. The insect powder is particularly suitable for the post-larval and/or adult stages.

The invention therefore relates quite particularly to an insect powder for use in the treatment of vibriosis in bivalves and decapods.

It also relates to an insect powder for use in the treatment of enteritis in shrimps.

In particular, the insect powder may be utilized for use in the treatment of shrimp early mortality syndrome/acute hepatopancreatic necrosis syndrome in shrimps.

Shrimp early mortality syndrome/acute hepatopancreatic necrosis syndrome in shrimps (known as "EMS/AHPNS") is responsible for a mortality rate exceeding 70% in shrimps infected with *Vibrio parahaemolyticus*.

When infected, the shrimp appears weak and disorientated. It sometimes has black lesions on its cuticle. Certain very virulent bacterial strains can decimate up to 80% of farmed shrimp such as the Asian tiger shrimp (*Penaeus monodon*) and Pacific white shrimp (*Penaeus vannamei*).

Advantageously, the insect powder used according to the invention comprises at least 67% by weight of proteins and at least 0.1% by weight chitin, percentages being given with respect to the total weight of insect powder.

By "proteins" is meant the quantity of crude proteins. The quantification of crude proteins is well known to a person skilled in the art. By way of example, the Dumas method or the Kjeldahl method may be mentioned. Preferably, the Dumas method, corresponding to the standard NF EN ISO 16634-1 (2008), is used.

Examples of such a powder are described in Examples 1 to 3 hereinafter.

Preferentially, the insect powder comprises 68% by weight of crude proteins, more preferentially 70% by weight of crude proteins, more preferentially 71% by weight of crude proteins, percentages by weight being given with respect to the total weight of insect powder.

According to the invention, by "chitin" is meant any type of chitin derivative, i.e. any type of polysaccharide derivative comprising N-acetyl-glucosamine units and D-glucosamine units, in particular the chitin-polypeptide copolymers (sometimes referred to as "chitin/polypeptide composite"). These copolymers can also be combined with pigments, often of the melanin type.

Chitin is thought to be the second most-synthesized polymer in the living world, after cellulose. In fact, chitin is synthesized by numerous species in the living world: it partly constitutes the exoskeleton of crustaceans and insects, and the lateral wall which surrounds and protects fungi. More particularly, in insects, chitin thus constitutes 3 to 60% of their exoskeleton.

The chitin content is determined by extraction thereof. Such a method can be the ADAC 991.43 method.

According to a first embodiment, the insect powder used according to the invention comprises at least 67% by weight proteins and at least 5% by weight chitin, percentages being given with respect to the total weight of insect powder.

Preferentially, this insect powder comprises between 5 and 16% by weight chitin, more preferentially between 8 and 14% chitin, percentages by weight being given with respect to the total weight of insect powder.

Advantageously, this insect powder has an ash content less than or equal to 4% by weight with respect to the total weight of insect powder, and even more advantageously, less than or equal to 3.5%.

Ash constitutes the residue resulting from the combustion of the composition according to the invention.

The method for determining the ash content is well known to a person skilled in the art. Preferably, the ash was determined according to the method laid down by EC Regulation 152/2009 of 27 Jan. 2009.

The fat content of this insect powder is preferably comprised between 5 and 20% by weight with respect to the total weight of insect powder, more preferentially between 9 and 17%.

The methods for determining the fat content are well known to a person skilled in the art. By way of example and in a preferred manner, this content will be determined according to the method of EC Regulation 152/2009.

Advantageously, the proteins of this insect powder have a digestibility greater than or equal to 85% by weight with respect to the total weight of crude proteins.

The digestibility is a pepsin digestibility measured by the method described in Directive 72/199/EC.

Preferably, the digestibility is greater than or equal to 86%, more preferentially greater than or equal to 88%.

Advantageously, this insect powder used according to the invention comprises between 35 and 65% by weight soluble proteins with respect to the total weight of proteins, and at least 50% of the soluble proteins have a size less than or equal to 12,400 g/mol.

By "total weight of proteins", is meant the weight of crude proteins present in the insect powder according to the invention.

By "soluble proteins", is meant, among the crude proteins, those which are soluble in an aqueous solution the pH of which is comprised between 6 and 8, advantageously between 7.2 and 7.6.

Preferably, the aqueous solution is a buffer solution the pH of which is comprised between 6 and 8, advantageously between 7.2 and 7.6. Preferentially, the buffer solution is an NaCl phosphate buffer solution, the pH of which is equal to 7.4+/−0.2.

Advantageously, this insect powder comprises between 38 and 60% by weight, preferably between 43 and 55% by weight soluble proteins with respect to the total weight of crude proteins.

Preferably, at least 60%, preferentially at least 70% of the soluble proteins have a size less than or equal to 12,400 g/mol.

More particularly, the soluble proteins have a size comprised between 6,500 and 12,400 g/mol.

Advantageously, less than 10%, preferably less than 8%, more preferentially less than 6% of soluble proteins have a size greater than or equal to 29,000 g/mol.

This insect powder can be prepared by a method comprising the following steps:
i) killing the insects,
ii) pressing the insects in order to obtain a press cake, and
iii) grinding the press cake.

The insects can be killed by scalding or blanching, as described in more detail hereinafter in Example 1.

Similarly, the pressing and grinding steps are described in more detail in this example.

Finally, the preparation method according to the invention can also comprise a step of drying the press cake.

The drying step is advantageously carried out after the pressing step and before the grinding step, and is also described in more detail hereinafter in Example 1.

According to a second embodiment, the insect powder used according to the invention comprises at least 71% by weight proteins and comprises between 0.1% and 2% by weight chitin, percentages being given with respect to the total weight of insect powder.

Preferably, this insect powder has a protein content greater than or equal to 72% by weight, more preferentially greater than or equal to 74% by weight, even more preferentially greater than or equal to 75% by weight, with respect to the total dry weight of powder.

More particularly, this powder has a chitin content comprised between 0.5 and 3% by weight, more preferentially comprised between 0.8 and 2% by weight, even more preferentially comprised between 0.8 et 1.7% by weight, with respect to the total dry weight of powder.

Preferably, this powder comprises between 5 and 20% by weight, preferably between 7 and 17% by weight of lipids, with respect to the total dry weight of powder.

More particularly, this powder comprises between 1 and 10% by weight, preferably between 2 and 6% by weight of ash, with respect to the total dry weight of powder.

Advantageously, the proteins of this insect powder have a digestibility greater than or equal to 85% by weight with respect to the total weight of crude proteins.

Preferably, the digestibility is greater than or equal to 88%, more preferentially greater than or equal to 92%.

This insect powder can be prepared by a method comprising the following steps:
killing the insects,
separating the cuticles from the soft part of the insects,
separating the soft part of the insects into a solid fraction, a fat fraction, and an aqueous fraction,
drying the solid fraction in order to obtain a dry solid fraction,
grinding the dry solid fraction in order to obtain an insect powder.

The insects can be killed by scalding or blanching, as described in more detail hereinafter in Example 1.

The cuticle is the outer layer (or exoskeleton) secreted by the epidermis of the insects. It is generally formed of three layers: the epicuticle, exocuticle and endocuticle.

By "soft part" is meant the flesh (in particular comprising the muscles and viscera) and the juice (comprising in particular the biological fluids, water and haemolymph) of the insects. In particular, the soft part does not consist of the juice of the insects.

Separating the cuticles from the soft part of the insects can be carried out using a filter press or a belt separator.

By "belt separator" is meant a device that comprises a squeezing belt (belt press filter) and a perforated drum.

Advantageously, in the present application, the insect powder is obtained from an insect species belonging to the order of the Coleoptera, preferably from the species *Tenebrio molitor*, regardless of the embodiment of the invention. The insect powder is then a beetle powder, and more particularly, a powder of *Tenebrio molitor*.

The invention therefore relates more particularly to a beetle powder, and in particular a powder of *Tenebrio molitor*, for use:
as a medicament,
in the treatment of vibriosis, in particular in bivalves and decapods,
in the treatment of enteritis of the shrimp, and/or
in the treatment of shrimp early mortality syndrome/acute hepatopancreatic necrosis syndrome in shrimps.

The invention also relates to a nutrition regime for molluscs and/or crustaceans, comprising at least 5% by weight of insect powder.

By "nutrition regime" is meant a set of nutrition ingredients (or constituents) in given proportions, intended to be consumed by the molluscs and/or crustaceans.

The insect powder can be used according to the invention as an alternative to the fishmeal generally administered in the nutrition regime of molluscs and crustaceans. It may replace fishmeal partially or totally. Preferentially, the insect powder replaces fishmeal at 50% or more, by weight fishmeal, even more preferentially at 75% or more, by weight fishmeal.

Substitution of the fishmeal by the insect powder advantageously makes it possible to boost the immune system of the molluscs and/or the crustaceans, in particular due to the high digestibility of the proteins and lipids of the insect powder. Moreover, this increases the density as well as the length of the intestinal villi, in particular in the white shrimp while increasing the size of the hepatocyte cells. Thus, this substitution of fishmeal by insect powder presents an alternative that is rich in proteins and lipids, not very expensive, and makes it possible to prevent and/or cure certain diseases such as shrimp vibriosis.

The nutrition regime administered to the molluscs or to the crustaceans advantageously comprises at least 10% by weight insect powder, preferentially at least 15% by weight insect powder, even more preferentially at least 25% by weight insect powder.

According to an advantageous embodiment of the invention, the nutrition regime administered to the molluscs or to the crustaceans comprises 20% by weight insect powder.

Preferentially, the insect powder totally replaces the fishmeal generally administered to the molluscs and to the crustaceans. Thus, the nutrition regime administered to the molluscs or to the crustaceans advantageously comprises 25% by weight insect powder.

This regime is particularly suitable for the shrimps, the other constituents of the regime, as well as their proportions, being defined in the manual "*Nutrient requirements of fish and shrimp*" published by the National Research Council (NRC) in 2011.

Advantageously, the nutrition regime according to the invention comprises an insect powder comprising at least 71% by weight proteins and comprising between 0.1 and 2% by weight chitin, percentages being given with respect to the total weight of insect powder.

Preferably, the insect powder is a beetle powder, more preferentially, a powder of *Tenebrio molitor*.

The invention also relates to the use of an insect powder comprising at least 67% by weight proteins and comprising at least 0.1% by weight chitin, percentages being given with respect to the total weight of insect powder, as a nutrition supplement in human or animal nutrition.

The insect powder used as a nutrition supplement in human or animal nutrition can comprise at least 67% by weight proteins and at least 5% by weight chitin, percentages being given with respect to the total weight of insect powder. This then is the insect powder of the first embodiment described above, including all the advantageous, particular and preferred characteristics, and the method for obtaining it.

Alternatively, the insect powder used as a nutrition supplement in human or animal nutrition can comprise at least 71% by weight proteins and comprise between 0.1% and 2% by weight chitin, percentages being given with respect to the total weight of insect powder. This then is the insect powder of the second embodiment described above, including all the advantageous, particular and preferred characteristics, and the method for obtaining it.

Advantageously, the insect powder is a beetle powder, more preferably, a powder of *Tenebrio molitor*.

Advantageously, the invention relates to the use of an insect powder, in particular those described above, as a nutrition supplement in the nutrition of the molluscs and/or crustaceans.

Finally, the invention relates to a nutrition supplement comprising an insect powder such as described above.

Advantageously, the insect powder is used as a nutrition supplement in the nutrition of shrimps, in particular farmed shrimps.

Other characteristics and advantages of the invention will become apparent from the following examples, given by way of illustration, with reference to.

EXAMPLE 1: METHOD FOR THE PREPARATION OF AN INSECT POWDER

The composition according to the invention is prepared from *Tenebrio molitor* larvae. Upon receipt of the larvae, the latter can be stored at 4° C. for 0 to 15 days in their rearing tanks without major degradation before being killed. The weight with respect to age of the larvae used is variable and as a result their composition can vary, as illustrated in Table 1 below:

TABLE 1

Biochemical composition of the larvae of *Tenebrio molitor* according to the weight thereof.

| | | Biomass (Insects) | | | | | |
|---|---|---|---|---|---|---|---|
| | mg | 23 | 35 | 58 | 80 | 108 | 154 |
| Dry matter | %* | 34 | 34 | 34.2 | 37.9 | 39.6 | 39.5 |
| Ash | %* | 1.59 | 1.52 | 1.6 | 1.75 | 1.67 | 1.43 |
| Crude protein | %* | 22.6 | 22.2 | 22 | 23.2 | 23.1 | 23.2 |
| Lipids | %* | 6.62 | 6.88 | 7.98 | 10.3 | 10.9 | 11.7 |

*The % s are expressed in dry weight with respect to the wet weight of larvae.

Step 1: Blanching the Insects

Living larvae (+4° C. to +25° C.) are conveyed in layers with a thickness comprised between 2 and 10 cm, on a perforated conveyor belt (1 mm) to a blanching chamber. The insects are thus blanched with steam (steam nozzles or bed) at 98° C. or with water at 100° C. (spray nozzles) or in mixed mode (water+steam). The residence time in the blanching chamber is comprised between 1 to 15 minutes, ideally 5 min.

The temperature of the larvae after blanching is comprised between 75° C. and 98° C.

Step 2: Pressing

Once blanched, the larvae are conveyed to the feed hopper of a continuous single-screw press. While passing into the press, the larvae are maintained at a temperature above 70° C. in order to increase the de-oiling yields. The principle of de-oiling is to pressurize the material inside a cylindrical cage by means of an arrangement of screws and rings arranged on the central shaft. The cage is lined inside with bars distributed in sections and kept apart by spaces of different thicknesses depending on the work area. The interstices thus arranged allow the flow of an oil fraction and limit the passage of the so-called "dry" matter, the protein fraction, which will be called "press cake", thus being involved in the pressurization.

The pressing yields obtained are comprised between 48 and 55%.

$$Y_{cake} = (mass_{cake}/mass_{juice} + mass_{cake})$$

The press cake obtained contains 35 to 40% dry matter, 67 to 75% proteins and 13 to 17% fats, percentages by weight being given with respect to the dry weight of press cake.

Step 3: Drying

The press cake is then arranged on a tray in a thin layer (approximately 2 cm) and is dried in ventilated/stirred air at 90° C. for 5 hours in order to obtain a press cake having a dry matter content greater than 92%.

This step makes it possible to guard against any contamination having occurred since the killing.

The Wa (water activity) after drying is 0.35. The microbiological results show an absence of *Salmonella* spp (method: IRIS *Salmonella* BKR 23/07-10/11) and Enterobacteria values less than 10 CFU/g (method: NF ISO 2128-2, December 2004, 30° C. and 37° C.).

Step 4: Grinding

The dried press cake, comprising mainly proteins, is finally ground using a continuous hammer mill (6 reversible moving parts—thickness 8 mm). The grinder is fed by a hopper with a flow rate control flap (180 kg/h). The perforated grill used to control the output granulometry is 0.8 mm. The speed of rotation of the motor is 3000 rpm (electric motorization, absorbed power 4 kW (5.5 CV)).

EXAMPLE 2: CHARACTERIZATION OF THE INSECT POWDER OBTAINED IN EXAMPLE 1

The insect powder prepared in Example 1 was characterized.

1. Analyses 1.1 Determination of the Moisture Content

The moisture content is determined according to the method originating from EC Regulation 152/2009 of 27 Jan. 2009 (103° C./4 h).

1.2 Determination of the Quantity of Crude Proteins

The crude proteins are determined according to the method called Dumas method, and corresponding to the standard NF EN ISO 16634-1 (2008).

1.3 Determination of the Quantity of Chitin

Dietary fibres from insect meal are essentially composed of chitin, the latter was therefore measured according to the ADAC 991.43 method. The values thus obtained are consequently slightly overestimated.

1.4 Determination of the Quantity of Fat

The fat was determined according to the method of EC Regulation 152/2009.

1.5 Determination of the Quantity of Ash

The crude ash was determined according to the method under EC Regulation 152/2009 of 27 Jan. 2009.

1.6 Determination of the Quantity of Phosphorus

The phosphorus is measured by ICP (induced coupled plasma) with internal calibration.

1.7 Determination of Energy

The energy value is obtained with the coefficients of EU Regulation 1169/201.

1.8 Determination of the Quantities of Amino Acids and Fatty Acids

This determination was carried out by gas chromatography after hydrolysis and derivatization of the amino acids and fatty acids respectively.

1.9 Determination of Pepsin Digestibility

The pepsin digestibility is measured by the method described in Directive 72/199/EC.

2. Results

The insect powder is detailed in Table 2 below.

TABLE 2

Composition of the insect powder

| | Unit | Composition |
|---|---|---|
| Macronutrient | | |
| Moisture | %* | 5.32 |
| Protein | %* | 67.09 |
| Chitin | %* | 8.0 |
| Fat | %* | 13.6 |
| Ash | %* | 3.21 |
| Total phosphorus | %* | 0.75 |
| Energy | MJ/kg | 23.74 |
| Amino acids | | |
| Arginine | %* | 2.56 |
| Histidine | %* | 1.39 |
| Isoleucine | %* | 2.11 |
| Leucine | %* | 3.99 |
| Lysine | %* | 3.32 |
| Threonine | %* | 1.87 |
| Valine | %* | 2.91 |
| Methionine | %* | 1.43 |
| Cysteine | %* | 0.63 |
| Phenylalanine | %* | 1.98 |
| Tyrosine | %* | 2.68 |
| Taurine | %* | 0.42 |
| Aspartic acid + asparagine | %* | 4.51 |
| Glutamic acid + glutamine | %* | 6.36 |
| Alanine | %* | 3.83 |
| Glycine | %* | 2.54 |
| Proline | %* | 3.18 |
| Serine | %* | 2.94 |
| Fatty acids | | |
| C12:0 | %* | 0.03 |
| C14:0 | %* | 0.22 |
| C15:0 | %* | 0.01 |
| C16:0 | %* | 1.33 |
| C16:1 | %* | 0.05 |
| C16:1n-7 | %* | 0.16 |
| C17:0 | %* | 0.02 |
| C17:1 | %* | 0.01 |
| C18:0 | %* | 0.35 |
| C18:1n-9 | %* | 3.03 |
| C18:1n-7 | %* | 0.04 |
| C18:2n-6 | %* | 2.96 |
| C18:2tn-6 | %* | 0.02 |
| C18:3n-3 | %* | 0.14 |
| C20:0 | %* | 0.02 |
| C20:1n-9 | %* | 0.01 |
| C20:2n-6 | %* | 0.01 |
| C22:0 | %* | 0.01 |

*Percentages by weight are expressed with respect to the total weight of powder composition. Moreover, a pepsin digestibility of 90 +/− 2% is obtained.

EXAMPLE 3: ALTERNATIVE METHOD FOR THE PREPARATION OF AN INSECT POWDER 200 g of *T. molitor* larvae are introduced into a beaker, placed in a water bath at 100° C. and containing 200 mL of water brought to the boil beforehand. After 5 minutes, the beaker is removed from the water bath, the larvae are drained, then mixed with a volume of water of 200 mL. The liquid thus obtained is passed into a twin-screw-type press. The press cake thus obtained is dried for 24 hours in an oven at 70° C., then ground to 250 µm. An insect powder is thus obtained.

EXAMPLE 4: EFFECTS OF THE INSECT POWDER OBTAINED IN EXAMPLE 1 ON THE WHITE SHRIMPS, IN PARTICULAR ON THEIR RESISTANCE TO THE PATHOGENIC BACTERIUM *VIBRIO PARAHAEMOLYTICUS*

Three experiments were conducted in order to assess the appetence of the insect powders in shrimps (Experiment 1), the digestibility of the proteins, the lipids and the energy of the insect powders in shrimps (Experiment 2) and the efficacy of the insect powder on the growth and the immunity of white shrimps (Experiment 3).

1. Material and Methods of the Experiments Conducted

The fishmeal used for all of these experiments is a fishmeal originating from Thailand and comprising a crude protein content of 56%, expressed with respect to the total weight of said fishmeal.

Similarly, the insect powder used is identical for all of these experiments and corresponds to the insect powder obtained in Example 1.

Statistics

These experiments were designed in a completely random manner (CMCA). All the data were analysed by ANOVA (variance analysis). Duncan's multiple-range test was used in order to determine the differences between the means of the different nutrition regimes. Alphabetical notation was used for marking the differences at an alpha 0.05 significance level. All research for Experiments 2 and 3 was conducted in the Aquatic Animal Food and Nutrition Laboratory, Department of Aquaculture, Faculty of Fisheries, Kasetsart University, Bangkok, Thailand.

Experiment 1: Test of Appetence of Insect Powders on White Shrimps with Respect to a Usual Nutrition Regime Constituted by 15% Fishmeal a. The Different Nutrition Regimes of the Experiment The attraction capacity of the insect powders to white shrimps was assessed in a completely random manner using the 5 following regimes, each repeated four times:
Regime 1 (R1): Control 30% fishmeal (hereinafter called FM);
Regime 2 (R2): Negative control 15% FM; 0% insect powder (hereinafter called INSM);
Regime 3 (R3): Negative control 10% FM; 5% INSM;
Regime 4 (R4): Negative control 5% FM; 10% INSM;
Regime 5 (R5): Negative control 0% FM; 15% INSM;
Four replicates of each regime were used in order to assess appetence.

b. Formulations and Production of the Nutrition Regimes

The regimes were formulated with ingredients that are useful in response to the known nutritional needs of white shrimps, described in particular in the reference manual of the National Research Council (NCR) published in 2011.

The insect powder used in the experimental nutrition regimes is that obtained in Example 1.

The attraction capacity of the insect powders to white shrimps was assessed in five nutrition regimes detailed below, the composition of which is presented in Table 3 below.

The approximate compositions of the feedstuffs tested such as the moisture, proteins, lipids, fibres, ash, were analyzed according to the description of the AOAC (2000) which is the international reference method.

TABLE 3

Compositions of the nutrition regimes of the white shrimps containing insect powder in place of fishmeal

| Ingredient of the formula | R1 INSM 0% –FM 30% | R2 INSM 0% –FM 15% | R3 INSM 5% –FM 10% | R4 INSM 10% –FM 5% | R5 INSM 15% –FM 0% |
|---|---|---|---|---|---|
| Fishmeal | 30.0 | 15.0 | 10.0 | 5.0 | 0.0 |
| Soya | 15.0 | 15.0 | 15.0 | 15.0 | 15.0 |
| Wheat gluten | 8.0 | 8.0 | 8.0 | 8.0 | 8.0 |
| Squid liver powder | 8.0 | 8.0 | 8.0 | 8.0 | 8.0 |
| Wheat flour | 24.0 | 24.0 | 24.0 | 24.0 | 24.0 |
| Broken rice | 2.2 | 1.2 | 1.2 | 1.2 | 1.2 |
| Soya protein concentrate | 0.0 | 15.0 | 15.0 | 15.0 | 15.0 |
| Insect powder | 0.0 | 0.0 | 5.0 | 10.0 | 15.0 |
| Maize gluten | 5.0 | 5.0 | 5.0 | 5.0 | 5.0 |
| Tunny fish oil | 0.5 | 0.5 | 0.5 | 0.5 | 0.5 |
| Soya oil | 2.0 | 2.0 | 2.0 | 2.0 | 2.0 |
| Soya lecithin | 2.0 | 2.0 | 2.0 | 2.0 | 2.0 |
| Mono-calcium phosphate | 0.0 | 1.0 | 1.0 | 1.0 | 1.0 |
| Binder | 1.7 | 1.7 | 1.7 | 1.7 | 1.7 |
| Pre-mix of vitamins | 1.6 | 1.6 | 1.6 | 1.6 | 1.6 |
| Total | 100.0 | 100.0 | 100.0 | 100.0 | 100.0 |
| Chemical composition by AOAC (2000) | | | | | |
| Moisture (%) | 7.38 | 7.14 | 7.09 | 7.25 | 7.18 |
| Proteins (%) | 37.38 | 36.88 | 37.06 | 37.84 | 38.81 |
| Lipids (%) | 7.18 | 6.50 | 6.97 | 7.23 | 7.60 |
| Fibre (%) | 2.69 | 2.95 | 3.09 | 3.33 | 3.68 |
| Ash (%) | 10.39 | 8.02 | 7.70 | 6.58 | 5.96 |
| Energy (Kcal/Kg) | 4560.14 | 4467.36 | 4477.59 | 4487.82 | 4498.05 | c. Nutrition Protocol of the White Shrimps

The white shrimps were fed with pellets containing 36% crude proteins and 7% crude lipids, at a quantity of approximately 5% of the average bodyweight of the shrimps/day (i.e. 1.5-2% bodyweight per feed) by placing the feedstuffs on a tray and providing 3 feeds per day.

For 10 days and only for the feed at 13.00 hours, the time necessary for the shrimps to ingest the feed initially, the number of shrimps reaching the food within the 15 minutes following deposit of the feedstuffs on the tray and the consumption of the feedstuffs per feed were recorded.

Four replicates of each regime were used in order to assess attraction capacity.

Unconsumed feed was collected from the tray one hour after its deposit and freeze-dried at −40° C., then weighed in order to determine the total nutrition consumption.

Over a study of 10 days, the food intake of each tray in each regime was calculated in order to determine the appetence, focussing on the time necessary for ingesting the feed, the quantity of feedstuffs consumed and the number of shrimps consuming the feedstuffs.

Experiment 2: Study of the Digestibility of the Proteins, the Lipids and the Energy of the Insect Powders in White Shrimps The in vivo digestibility of the proteins, the lipids and the energy of the insect powder in white shrimps were determined by an indirect method. Three hundred shrimps with an average weight of 5 to 8 g were randomly distributed in each of the twenty aquariums. Ten repetitions with ten shrimps, each fed with a reference nutrition regime composed of 25% fishmeal and 5% squid meal, 63.7% wheat flour, gluten and soya isolate and soya lecithin, 3% mixture of tunny oil and soya oil, 3.3% premix of vitamins and 1% chromic oxide as digestibility marker.

Another nutrition regime was provided to the other 200 shrimps (20 repetitions of 10 shrimps), composed of 30% insect powder plus 1% chromic oxide as marker, 63.7% wheat flour, gluten and soya isolate and soya lecithin, 3% of a mixture of tunny oil and soya oil, 3.3% of premix of vitamins and 1% of chromic oxide as digestibility marker.

The acclimatization period was one week. After this period, the shrimps were fed with the allocated nutrition regimes in excess (4%) three times per day. Two hours after the feed, the aquariums were cleaned, and half an hour before the following feed, the faecal matter was collected, for 1 to 2 weeks.

The samples originating from each nutrition regime were collected together at the end of the experiment, so as to have enough material for analysis. They were dried in a hot air oven at 65° C. The samples of the feedstuffs and the faecal matter were analyzed for lipids and proteins (AOAC, 2000). The chromic oxide was determined (Scott, 1978). The apparent digestibility coefficient (ADC) was calculated as described by Cho et al. (1985).

Apparent digestibility coefficient (ADC %)=100−(Indicator in the nutrition regime in %)/Indicator in the faecal matter in %

Apparent digestibility coefficient of nutrients (ADC Nu %)=100−(Indicator in the nutrition regime in % $X$ nutrients in the faecal matter in %)/Indicator in the faecal matter in % $X$ nutrients in the nutrition regime in c/o)

Experiment 3: Efficacy of the Insect Powder on the Growth Performance and the Immunity of White Shrimps (Litopenaeus vanammei)

a. Design of the Tests

The experiment was designed in a completely random manner (CMCA) with 5 regimes with 4 replicates.

The different nutrition regimes are indicated in Table 4 below.

TABLE 4

The different nutrition regimes

| Nutrition regime | Description | Level of fishmeal in the nutrition regime | Insect powder replacing the fishmeal proteins |
|---|---|---|---|
| T1 | INSM replaces 0% of FM | 25% | 0% |
| T2 | INSM replaces 25% of FM | 18.75% | 25% (5.15% INSM) |
| T3 | INSM replaces 50% of FM | 12.5% | 50% (10.30% INSM) |
| T4 | INSM replaces 75% of FM | 6.25% | 75% (15.40% INSM) |
| T5 | INSM replaces 100% of FM | 0% | 100% (20.50% INSM) |

The experiment was carried out in 20 glass aquariums each having 100 litres capacity, with 70 litres of salt water at 15 ppt (parts per trillion). Juvenile white shrimps (approx. 3 to 4 g) were stocked at a density of 40 shrimps/m$^2$ (10 per aquarium). The insect powder was mixed into the nutrition while the fish oil was gradually reduced. The feedstuffs thus prepared were provided to the shrimps 3 times per day at a quantity comprised between 3 and 5% of the average bodyweight of the shrimps for 8 weeks. Every 2 to 3 days, the feed waste was siphoned off and 15-20% of the water renewed.

The ingredients of the different nutrition regimes were ground to 150-250 microns, mixed together, then 25% water was added before passing through the Hobart chopper. The pellets thus obtained were dried in a hot air oven.

The approximate compositions of the nutrition regimes tested such as the moisture, proteins, lipids, fibres, ash and energy were analyzed according to the description of AOAC (2000). This chemical composition as well as the composition of ingredients are summarized in Table 5 below.

TABLE 5

Composition of the experimental nutrition regimes

| Matter | T1 INSM replaces 0% of FM | T2 INSM replaces 25% of FM | T3 INSM replaces 50% of FM | T4 INSM replaces 75% of FM | T5 INSM replaces 100% of FM |
|---|---|---|---|---|---|
| Fishmeal | 25 | 18.75 | 12.5 | 6.25 | 0 |
| Soya | 25 | 25 | 25 | 25 | 25 |
| Wheat gluten | 10 | 10 | 10 | 10 | 10 |
| Liver powder | 5 | 5 | 5 | 5 | 5 |
| Wheat flour | 26.7 | 26.6 | 26.65 | 26.15 | 25.55 |
| Insect powder | 0 | 5.15 | 10.3 | 15.4 | 20.5 |
| Tunny fish oil | 2 | 2 | 2 | 2 | 2 |
| Soya oil | 1 | 0.85 | 0.75 | 0.65 | 0.55 |
| Soya lecithin | 2 | 2 | 2 | 2 | 2 |
| Lysine | 0 | 0.1 | 0.2 | 0.3 | 0.4 |
| Methionine | 0 | 0.05 | 0.1 | 0.15 | 0.2 |
| Monocalcium phosphate | 0 | 1.2 | 2.2 | 3.3 | 4.5 |
| Limestone rock/oyster shell | 0 | 0 | 0 | 0.5 | 1 |
| Carbamide | 1.7 | 1.7 | 1.7 | 1.7 | 1.7 |
| Pre-mix of vitamins | 1.6 | 1.6 | 1.6 | 1.6 | 1.6 |
| Total | 100.00 | 100.00 | 100.00 | 100.00 | 100.00 |
| Chemical composition by AOAC (2000) | | | | | |
| Moisture (%) | 9.38 | 8.82 | 8.75 | 9.02 | 9.45 |
| Proteins (%) | 35.30 | 35.66 | 35.73 | 36.39 | 36.37 |
| Lipids (%) | 7.18 | 7.16 | 7.18 | 7.06 | 7.06 |
| Fibre (%) | 2.86 | 2.86 | 2.85 | 2.79 | 2.78 |
| Ash (%) | 8.25 | 8.02 | 7.35 | 6.65 | 6.03 |
| Energy (Kcal/Kg) | 4470.38 | 4434.08 | 4404.79 | 4362.88 | 4318.97 | b. Parameters

The data necessary for this experiment relate to the growth performance of the shrimps under test conditions. These include:

Growth Performance

The live weight or average weight of the shrimp, the weight gain

The specific growth rate (SGR: {(Ln weight Week 8)−(Ln weight Week 0)}×100)/(period of culture in days)

The feed conversion rate (FCR: feed consumption/shrimp production)

Survival (according to the usual laboratory research method)/mortality rate

Immune Status

The immune status is determined at the end of the study by counting the haemocyte total, the phenol-oxydase activity, the haemolymph proteins.

number of shrimps consuming the feedstuffs do not differ significantly between the different nutrition regimes (p>0.05). The daily nutrition consumption per feed of the shrimps fed with 30% fishmeal (R1) appears to be stable, while the groups of shrimps fed with 15% fishmeal with and without insect powder of *Tenebrio molitor* (R2-R5) show a wide variation in the consumption of feedstuffs per feed. The time necessary for the shrimps to start consumption of the feedstuffs and the number of shrimps consuming the feedstuffs are completely stable after five days of the study. These elements may mean that the feed based on insect powder of *Tenebrio molitor* did not show greater attraction in the nutrition regimes of the white shrimps. In addition, this also demonstrates that the reduction in fishmeal in the nutrition regimes of the white shrimps does not have a significant effect on the nutrition consumption by the shrimps.

TABLE 6

Attraction capacity of the feed based on insect powder in the nutrition regime of white shrimps with a rate of inclusion of 15% in fishmeal

| Attraction | R1 INSM 0% −FM 30% | R2 INSM 0% −FM 15% | R3 INSM 5% −FM 10% | R4 INSM 10% −FM 5% | R5 INSM 15% −FM 0% | P-value |
|---|---|---|---|---|---|---|
| Nutrition consumption (g per feed) | 1.32 | 1.25 | 1.18 | 1.12 | 1.19 | 0.340 |
| Start time of consumption of feedstuffs (seconds) | 31.35 | 30.18 | 27.35 | 31.13 | 28.78 | 0.685 |
| Number of shrimps consuming feedstuffs within 15 minutes | 5.40 | 5.28 | 4.85 | 4.38 | 4.80 | 0.307 |

Morphology of the Intestinal Villi and Hepatopancreas.

At the end of the study, histopathology of the intestinal villi and hepatopancreas was carried out.

Test of Resistance to the Pathogen *Vibrio parahaemolyticus*.

The resistance of the Pacific white shrimps to *Vibrio parahaemolyticus* was studied in order to determine the ability of the shrimps to resist the pathogenic bacteria.

After having fed the shrimps with an experimental nutrition regime for 8 weeks, thirty shrimps on each regime were sampled and were the subject of an injection of pathogens, namely the bacterium *Vibrio parahaemolyticus*, 4.3/105 CFU (colony-forming unit)/ml (4.6 log CFU/ml) injected intramuscularly. The mortality was recorded for 10 days. The bacteria reduction capacity was determined.

2. Results of Experiments 1, 2 and 3

Results of Experiment 1

The appetence of the insect powder in the nutrition regime of the white shrimp (*Litopenaeus vannamei*) was studied, focussing on the start time of consumption of the feedstuffs by the shrimps, the number of shrimps consuming the feedstuffs within 15 minutes and the quantity of feedstuffs consumed during the feed observed. The results of the attraction capacity of the insect powder have been presented in Table 6 below. The attraction capacity, in terms of the quantity of feedstuffs consumed during the feed observed, the start time of consumption of the feedstuffs and the Results of Experiment 2

The in vivo digestibility of the insect powder of *Tenebrio molitor* in white shrimps was determined by the indirect method according to Cho et al. (1985). The apparent digestibility of nutrients is presented in Table 7 below. The results indicate that the insect powder of *Tenebrio molitor* has a high proteins and lipids content and an energy digestibility of 96 to 97%.

TABLE 7

Apparent digestibility of the nutrients in the insect powder according to Example 1 (average ± TE).

| Apparent digestibility | Insect powder |
|---|---|
| Digestibility of proteins (%) | 97.47 + 1.66 |
| Digestibility of lipids (%) | 97.85 + 0.36 |
| Energy digestibility (%) | 96.05 + 1.20 |

Results of Experiment 3

Efficacy of the Insect Powder on the Performance of White Shrimps

Figure 1:
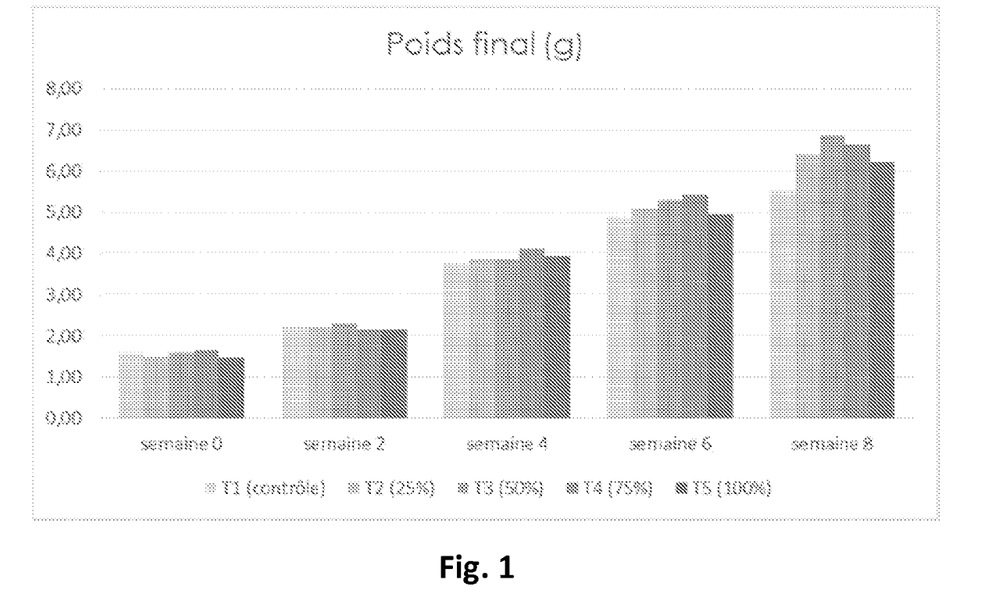
FIG. 1 is a diagram showing the final weight of the white shrimps fed according to different nutrition regimes, either including or not including insect powder in place of fishmeal.
Figure 2:
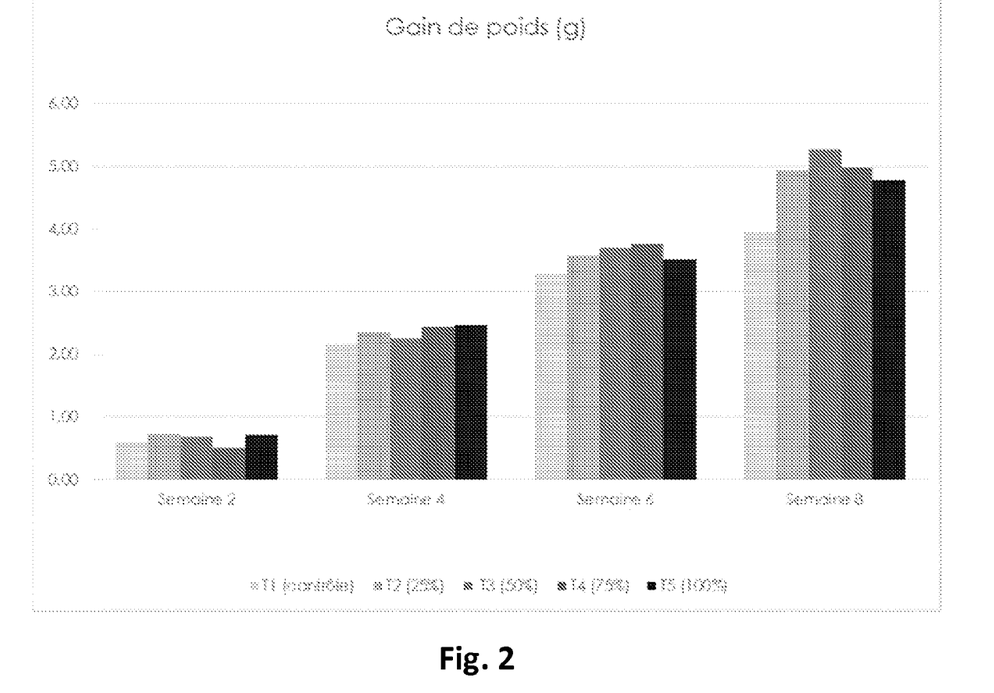
FIG. 2 is a diagram showing the weight gain of the white shrimps fed according to different nutrition regimes, either including or not including insect powder in place of fishmeal.

The effects of the insect powder on the performance of white shrimps (*L. vannamei*) were studied for 8 weeks. The results on the growth performance of the shrimps were presented in Table 8, as well as in FIGS. 1 and 2. The results showed that from the 8th week, the growth performance of the shrimps in terms of final weight, weight gain, average daily gain and specific growth rate were significantly greater with respect to the control (p<0.05). The shrimps fed with insect powder had a better growth rate than the control (said control having 25% fishmeal, without a supplement of insect powder). The nutrition consumption over the 8 weeks was however not significantly different (p>0.05). Nor was the survival rate over 8 weeks significantly different (p>0.05). The feed conversion rate was significantly lower from week 8 for T2-T5 with respect to the control regime (p<0.05). The protein efficiency ratio is not significantly different (p>0.05).

Consequently, the insect powder may promote the growth rate of shrimps in a nutrition regime reducing fishmeal up to a replacement of 100% (rate of inclusion of fishmeal 25% in the control regime). The reason is the high digestibility of the proteins and lipids of the insect powder.

TABLE 8

Growth performance of the white shrimps fed with a nutrition regime comprising insect powder in place of fishmeal and comparison with the control (without insect powder).

| Growth performance | Periods | T1 INSM replaces 0% of FM | T2 INSM replaces 25% of FM | T3 INSM replaces 50% of FM | T4 INSM replaces 75% of FM | T5 INSM replaces 100% of FM | P-value |
|---|---|---|---|---|---|---|---|
| Production (g/aquarium) | 0 weeks | 24.03 $^a$ | 22.48 $^a$ | 24.00 $^a$ | 24.95 $^a$ | 21.87 $^a$ | 0.094 |
| | 2 weeks | 32.33 $^a$ | 32.48 $^a$ | 33.73 $^a$ | 32.18 $^a$ | 32.12 $^a$ | 0.910 |
| | 4 weeks | 53.28 $^a$ | 55.10 $^a$ | 54.75 $^a$ | 59.62 $^a$ | 56.13 $^a$ | 0.493 |
| | 6 weeks | 62.75 $^a$ | 65.52 $^a$ | 68.82 $^a$ | 72.30 $^a$ | 63.20 $^a$ | 0.340 |
| | 8 weeks | 63.77 $^b$ | 72.22 $^{ab}$ | 79.00 $^a$ | 78.55 $^a$ | 71.62 $^{ab}$ | 0.025 |
| Number of shrimps (per aquarium) | 0 weeks | 10 | 10 | 10 | 10 | 10 | / |
| Final weight (g/individual) | 0 weeks | 1.60 $^a$ | 1.50 $^a$ | 1.60 $^a$ | 1.66 $^a$ | 1.46 $^a$ | 0.098 |
| | 2 weeks | 2.21 $^a$ | 2.22 $^a$ | 2.29 $^a$ | 2.17 $^a$ | 2.17 $^a$ | 0.831 |
| | 4 weeks | 3.76 $^a$ | 3.86 $^a$ | 3.85 $^a$ | 4.11 $^a$ | 3.93 $^a$ | 0.662 |
| | 6 weeks | 4.88 $^a$ | 5.08 $^a$ | 5.29 $^a$ | 5.42 $^a$ | 4.97 $^a$ | 0.537 |
| | 8 weeks | 5.54 $^b$ | 6.43 $^a$ | 6.87 $^a$ | 6.65 $^a$ | 6.23 $^{ab}$ | 0.030 |
| Weight gain (g/individual) | 2 weeks | 0.60 $^a$ | 0.72 $^a$ | 0.69 $^a$ | 0.51 $^a$ | 0.71 $^a$ | 0.213 |
| | 4 weeks | 2.16 $^a$ | 2.36 $^a$ | 2.25 $^a$ | 2.45 $^a$ | 2.47 $^a$ | 0.592 |
| | 6 weeks | 3.28 $^a$ | 3.58 $^a$ | 3.69 $^a$ | 3.76 $^a$ | 3.51 $^a$ | 0.665 |
| | 8 weeks | 3.94 $^b$ | 4.93 $^a$ | 5.27 $^a$ | 4.99 $^a$ | 4.77 $^a$ | 0.021 |
| Daily weight gain (g/individual/day) | 2 weeks | 0.04 $^a$ | 0.05 $^a$ | 0.05 $^a$ | 0.04 $^a$ | 0.05 $^a$ | 0.019 |
| | 4 weeks | 0.08 $^a$ | 0.08 $^a$ | 0.08 $^a$ | 0.09 $^a$ | 0.09 $^a$ | 0.628 |
| | 6 weeks | 0.08 $^a$ | 0.09 $^a$ | 0.09 $^a$ | 0.09 $^a$ | 0.08 $^a$ | 0.672 |
| | 8 weeks | 0.07 $^b$ | 0.09 $^a$ | 0.09 $^a$ | 0.09 $^a$ | 0.09 $^a$ | 0.007 |
| Specific growth rate (%/day) | 2 weeks | 2.29 $^a$ | 2.81 $^a$ | 2.56 $^a$ | 1.88 $^a$ | 2.82 $^a$ | 0.087 |
| | 4 weeks | 3.05 $^a$ | 3.38 $^a$ | 3.12 $^a$ | 3.24 $^a$ | 3.52 $^a$ | 0.254 |
| | 6 weeks | 2.66 $^a$ | 2.89 $^a$ | 2.84 $^a$ | 2.81 $^a$ | 2.91 $^a$ | 0.577 |
| | 8 weeks | 2.22 $^b$ | 2.59 $^a$ | 2.60 $^a$ | 2.47 $^a$ | 2.59 $^a$ | 0.016 |
| Nutrition consumption (g/individual) | 2 weeks | 0.53 $^a$ | 0.50 $^a$ | 0.53 $^a$ | 0.55 $^a$ | 0.48 $^a$ | 0.097 |
| | 4 weeks | 1.67 $^a$ | 1.63 $^a$ | 1.72 $^a$ | 1.65 $^a$ | 1.60 $^a$ | 0.695 |
| | 6 weeks | 4.04 $^a$ | 4.04 $^a$ | 4.07 $^a$ | 4.15 $^a$ | 4.14 $^a$ | 0.977 |
| | 8 weeks | 6.17 $^a$ | 6.40 $^a$ | 6.26 $^a$ | 6.46 $^a$ | 6.27 $^a$ | 0.975 |
| Daily nutrition consumption (g/individual/day) | 2 weeks | 0.04 $^a$ | 0.04 $^a$ | 0.04 $^a$ | 0.04 $^a$ | 0.03 $^a$ | 0.068 |
| | 4 weeks | 0.06 $^a$ | 0.06 $^a$ | 0.06 $^a$ | 0.06 $^a$ | 0.06 $^a$ | 0.605 |
| | 6 weeks | 0.10 $^a$ | 0.10 $^a$ | 0.10 $^a$ | 0.10 $^a$ | 0.10 $^a$ | 0.946 |
| | 8 weeks | 0.11 $^a$ | 0.11 $^a$ | 0.11 $^a$ | 0.12 $^a$ | 0.11 $^a$ | 0.985 |
| Nutrition conversion rate | 2 weeks | 0.90 $^a$ | 0.80 $^a$ | 0.84 $^a$ | 1.21 $^a$ | 0.69 $^a$ | 0.119 |
| | 4 weeks | 0.78 $^a$ | 0.71 $^a$ | 0.78 $^a$ | 0.68 $^a$ | 0.66 $^a$ | 0.270 |
| | 6 weeks | 1.24 $^a$ | 1.16 $^a$ | 1.11 $^a$ | 1.13 $^a$ | 1.20 $^a$ | 0.683 |
| | 8 weeks | 1.59 $^a$ | 1.32 $^b$ | 1.20 $^b$ | 1.30 $^b$ | 1.32 $^b$ | 0.052 |
| Survival rate (%) | 2 weeks | 97.78 $^a$ | 97.78 $^a$ | 97.78 $^a$ | 98.89 $^a$ | 98.89 $^a$ | 0.924 |
| | 4 weeks | 94.44 $^a$ | 95.56 $^a$ | 94.44 $^a$ | 96.67 $^a$ | 95.56 $^a$ | 0.909 |
| | 6 weeks | 85.56 $^a$ | 86.67 $^a$ | 86.67 $^a$ | 88.89 $^a$ | 84.44 $^a$ | 0.719 |
| | 8 weeks | 76.67 $^a$ | 75.56 $^a$ | 76.67 $^a$ | 78.89 $^a$ | 76.67 $^a$ | 0.896 |
| Protein efficiency ratio | 10 weeks | 1.80 $^a$ | 2.13 $^a$ | 2.33 $^a$ | 2.12 $^a$ | 2.06 $^a$ | 0.106 |

Comment: The means with the same exponents within the rows are not significantly different (p ≥ 0.05).

Immunity of the Shrimps

The immunity of the shrimps under normal conditions was studied over 8 weeks of experiment. The results presented in Table 9 have shown that there was no significant difference with respect to the control (p>0.05) on the total number of haemocytes, the protein content of the haemolymph and the phenol-oxidase activity. Consequently, insect powder can replace fishmeal up to 100% (rate of inclusion of fishmeal 25% in the nutrition formula) without any undesirable effect on the immunity of the shrimps.

Figure 3:
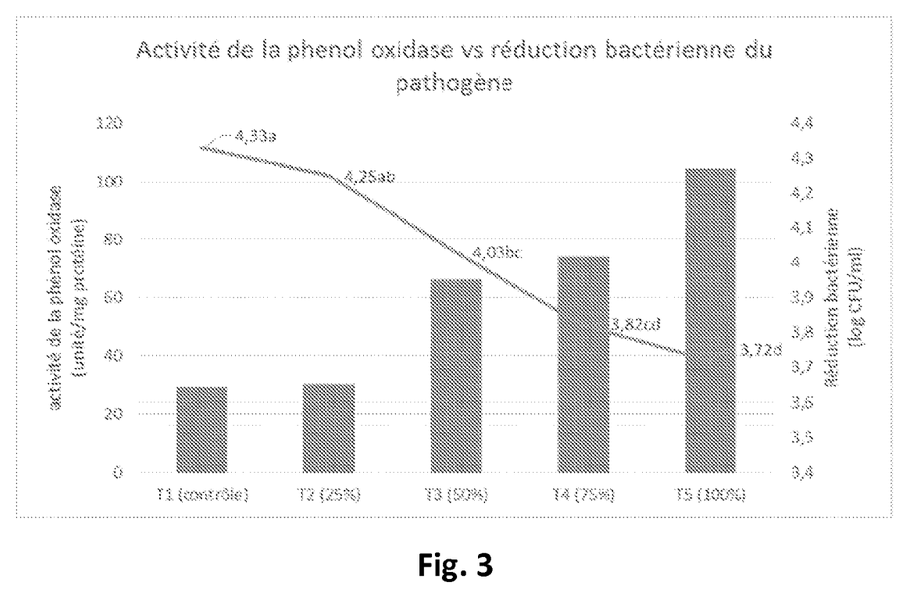
FIG. 3 is a diagram showing the activity of phenol oxidase as a function of the bacterial reduction of the pathogen, in white shrimps infected with *Vibrio parahaemolyticus* and fed according to different nutrition regimes, either including or not including insect powder in place of fishmeal.

The resistance status after injection of *Vibrio parahemolyticus* is studied over 6 hours. The immunity of the shrimps in Table 9 shows a high (p<0.05) activity of phenol-oxidase in the group of shrimps fed with the insect powder replacing 50 to 100% of the fishmeal (rate of inclusion of the fishmeal in the nutrition regime from 10.3 to 20.6%). More particularly, in FIG. 3, a negative correlation is noted between the presence of bacteria and phenol oxidase activity. In addition, there is a strong negative correlation between the reduction of bacteria and increasing inclusion of insect powder in the nutrition regime (p<0.05).

TABLE 9

Immunity of the white shrimps fed with insect powder of *Tenebrio molitor* as replacement for fishmeal and comparison with the control (without insect powder).

| Immunity | Status | T1 INSM replaces 0% of FM | T2 INSM replaces 25% of FM | T3 INSM replaces 50% of FM | T4 INSM replaces 75% of FM | T5 INSM replaces 100% of FM | P-value |
| --- | --- | --- | --- | --- | --- | --- | --- |
| Total number of haemocytes ($\times 10^6$ cells/ml) | Normal | $1.01^a$ | $1.24^a$ | $1.16^a$ | $1.28^a$ | $1.31^a$ | 0.160 |
| | Injection | $0.89^a$ | $1.16^a$ | $1.03^a$ | $1.16^a$ | $1.10^a$ | 0.299 |
| Protein content of the haemolymph (g/dl) | Normal | $4.54^a$ | $5.71^a$ | $4.93^a$ | $6.24^a$ | $6.01^a$ | 0.674 |
| | Injection | $5.83^a$ | $6.21^a$ | $4.99^a$ | $3.53^a$ | $4.06^a$ | 0.066 |
| Phenol-oxidase activity (unit/mg protein) | Normal | $113.24^a$ | $141.70^a$ | $135.43^a$ | $137.93^a$ | $121.98^a$ | 0.961 |
| | Injection | $29.29^c$ | $30.24^c$ | $66.29^b$ | $74.32^{ab}$ | $104.64^a$ | 0.002 |
| Bacteria reduction capacity (or clearance) (Log UFC/ml) | Injection | $4.33^a$ | $4.25^{ab}$ | $4.03^{bc}$ | $3.82^{cd}$ | $3.72^d$ | 0.001 |

Comment: The means with the same exponents within the rows are not significantly different (p ≥ 0.05).

Mortality of the Shrimps

Figure 4:
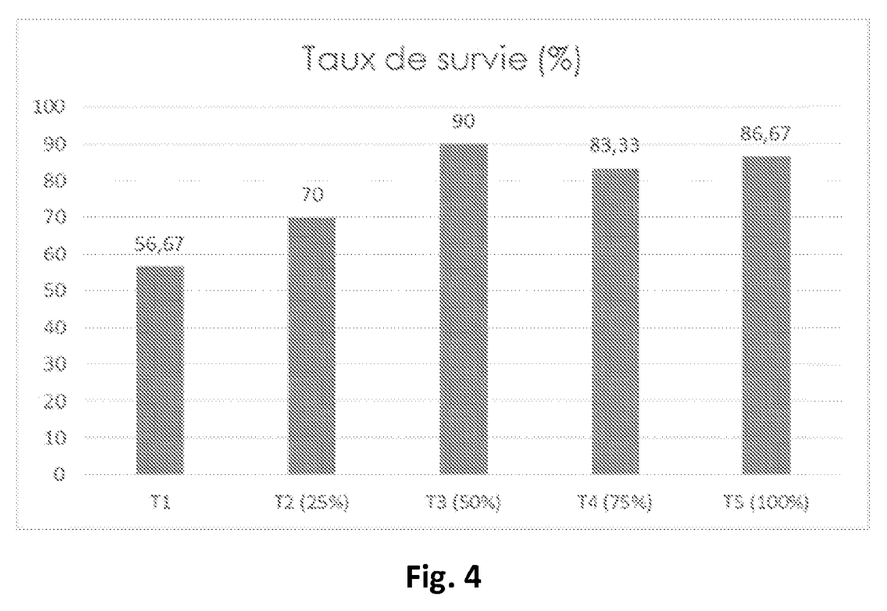
FIG. 4 is a diagram showing the survival rate of the shrimps infected with *Vibrio parahaemolyticus* as a function of the nutrition regime provided, either including or not including insect powder in place of fishmeal.

The mortality of the shrimps after exposure to *Vibrio parahaemolyticus*, $4.3 \times 10^5$ ufc/ml, has been presented in Table 10, as well as in FIG. 4. The shrimps fed with nutrition regimes in which fishmeal was reduced (by 50 to 100%) and supplemented by insect powder of *Tenebrio molitor* (replacing fishmeal by 50 to 100%) showed a significantly lower mortality rate (P<0.05) than the control nutrition regime with 25% fishmeal (T1) and than the group of shrimps fed with nutrition regimes in which the fishmeal was reduced and supplemented by insect powder (25% fishmeal replaced). This may result from the high lipid and protein digestibility of the insect powder and from a possible better quality of the lipids with respect to soya oil, allowing the shrimps to obtain more nutriments.

TABLE 10

Cumulative mortality rate after injection of the pathogen *Vibrio parahaemolyticus* in white shrimps fed with nutrition regimes comprising insect powder in place of fishmeal and comparison with the control (without insect powder)

| Day(s) after injection of the pathogen | T1 INSM replaces 0% of FM | T2 INSM replaces 25% of FM | T3 INSM replaces 50% of FP | T4 INSM replaces 75% of FM | T5 INSM replaces 100% of FM | P-value |
| --- | --- | --- | --- | --- | --- | --- |
| Day 1 | 0.00 | 0.00 | 0.00 | $0.00^{ab}$ | 0.00 | * |
| Day 2 | $10.00^a$ | $3.33^{ab}$ | $0.00^b$ | $6.67^{ab}$ | $0.00^b$ | 0.029 |
| Day 3 | $23.33^a$ | $13.33^{ab}$ | $3.33^b$ | $13.33^{ab}$ | $3.33^b$ | 0.008 |
| Day 4 | $30.00^a$ | $23.33^{ab}$ | $6.67^b$ | $13.33^{ab}$ | $10.00^b$ | 0.048 |
| Day 5 | $40.00^a$ | $30.00^{ab}$ | $10.00^b$ | $13.33^{ab}$ | $13.33^{ab}$ | 0.014 |
| Day 6 | $40.00^a$ | $30.00^{ab}$ | $10.00^b$ | $13.33^{ab}$ | $13.33^{ab}$ | 0.014 |
| Day 7 | $40.00^a$ | $30.00^{ab}$ | $10.00^c$ | $16.67^{bc}$ | $13.33^{bc}$ | 0.017 |
| Day 8 | $40.00^a$ | $30.00^{ab}$ | $10.00^c$ | $16.67^{bc}$ | $13.33^{bc}$ | 0.017 |
| Day 9 | $40.00^a$ | $30.00^{ab}$ | $10.00^c$ | $16.67^{bc}$ | $13.33^{bc}$ | 0.017 |
| Day 10 | $43.33^a$ | $30.00^{ab}$ | $10.00^c$ | $16.67^{bc}$ | $13.33^{bc}$ | 0.005 |
| Mortality rate (%) | $43.33^a$ | $30.00^{ab}$ | $10.00^c$ | $16.67^{bc}$ | $13.33^{bc}$ | 0.005 |
| Survival rate (%) | $56.67^c$ | $70.00^{bc}$ | $90.00^a$ | $83.33^{ab}$ | $86.67^{ab}$ | 0.005 |

Comment: The means with the same exponents within the rows are not significantly different (p ≥ 0.05).
* no statistical analysis, the value is the same.

Histology of the Hepatopancreas and the Intestinal Villi of the Shrimps

The hepatopancreatic histology of the shrimps fed with the control nutrition regime and the regimes with the insect powder showed larger B cells and R cells. These cells produce nutriment regulation enzymes. In the nutrition regimes T2-T5, the B (secretory) and R (reserve) cells enlarged more than in the control regime T1. This means that the hepatocyte cells, having accumulated more nutrients, can be reserves of glycogen and/or lipids, as a result of the high protein or lipid digestibility of the insect powder. The density and length of intestinal villi were high under all the nutrition regimes.

3. Conclusion

Insect powder, in particular from *Tenebrio molitor*, can replace fishmeal, up to 100% replacement of the fishmeal, without any negative effect on the growth performance, the health of the shrimps and the histology of the hepatopancreas and the intestinal villi in small-sized shrimps (1-5 g) with an equivalent nutritional profile between the nutrition regimes comprising fishmeal and/or insect powder. When the insect powder replaces between 25 and 100% of the fishmeal in the nutrition regime in shrimps during more than 6 weeks, the shrimp may have the best growth rate and a high digestibility. The group of shrimps fed with insect powder from *Tenebrio molitor* as replacement for fishmeal at 50 or 100% showed a better resistance to the pathogen *Vibrio parahaemolyticus*.

The invention claimed is:

1. A method for treating vibriosis and/or symptoms thereof in an animal subject in need thereof, by administering to said animal a composition comprising a therapeutically effective amount of beetle powder, wherein the animal is not a crab.

2. The method according to claim 1, wherein said subject is a bivalve or a decapod.

3. The method according to claim 2, wherein administering the beetle powder treats shrimp enteritis.

4. The method to claim 3, wherein administering the beetle powder treats shrimp early mortality syndrome/acute hepatopancreatic necrosis syndrome in shrimps.

5. The method according to claim 1, wherein said beetle powder comprises at least 67% by weight proteins and at least 0.1% by weight chitin, percentages being given with respect to the total weight of beetle powder.

6. The method according to claim 5, wherein said beetle powder comprises at least 67% by weight proteins and at least 5% by weight chitin, percentages being given with respect to the total weight of beetle powder.

7. The method according to claim 5, wherein said beetle powder comprises at least 71% by weight proteins and comprises between 0.1 and 2% by weight chitin, percentages being given with respect to the total weight of beetle powder.

8. The method according to claim 1, wherein said beetle powder is obtained from the species *Tenebrio molitor*.

* * * * *